(12) United States Patent  (10) Patent No.: US 7,981,118 B2
Mommaerts  (45) Date of Patent: *Jul. 19, 2011

(54) APPARATUS FOR INTRAORAL DISTRACTION OSTEOTOMY TO WIDEN THE UPPER JAW

(75) Inventor: Maurice Yves Mommaerts, Sint Martens-Latern (BE)

(73) Assignee: Synthes USA, LLC, West Chester, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/537,919

(22) Filed: Aug. 7, 2009

(65) Prior Publication Data

US 2010/0160920 A1    Jun. 24, 2010

Related U.S. Application Data

(63) Continuation of application No. 11/070,862, filed on Mar. 2, 2005, now Pat. No. 7,588,579, which is a continuation-in-part of application No. 10/193,695, filed on Jul. 11, 2002, now abandoned, which is a continuation of application No. PCT/EP01/00398, filed on Jan. 11, 2001.

(51) Int. Cl.
  *A61B 17/66* (2006.01)
(52) U.S. Cl. ............. 606/105; 606/282; 606/90; 606/57
(58) Field of Classification Search ............... 606/54–59, 606/252, 257, 258, 90, 105, 282
  See application file for complete search history.

(56) References Cited

U.S. PATENT DOCUMENTS 360,695 A    7/1887  Holmes
(Continued)

FOREIGN PATENT DOCUMENTS

AT    192049    9/1957
(Continued)

OTHER PUBLICATIONS

"Malleable". Merriam-Webster Online Dictionary [online], [retrieved on Nov. 9, 2006], Retrieved from the internet <URL: www.m-w.com.

(Continued)

*Primary Examiner* — Eduardo C Robert
*Assistant Examiner* — Jerry Cumberledge
(74) *Attorney, Agent, or Firm* — Woodcock Washburn LLP

(57) ABSTRACT

The present invention provides an improved orthopaedic system for the modification of the distance between the contralateral maxillary segments or halves. In a preferred embodiment, the system includes two metal bone plates fixed on the bony palatal shelves, with slotted extensions which opposite internal walls have concave indents into which disk-shaped wings of interchangeable distraction modules fit. The in the palatal plane concave female indent and the convex male wing prevent distraction module dislocation in case of oblique placement in the axial plane. In the frontal plane, the male wings are straight.

The extension on the abutment plate has a slit like opening at the caudal side, to be fitted by a suture or a wire of any kind material, passing also in an opening in the male wing of the distraction module, to allow for assembling the units before fixation in the bony palatal shelve.

The abutment plate is made partly malleable for an improved accommodation to the local alveolar bony anatomy.

The opposing ends of the abutment plate have a shape allowing the anterior side to slip under the mucoperiosteum similar to a dissecting instrument, and the posterior end rounded and blunt in a way to protect the palatal arterioles.

The abutment plates are provided by a slotted hole or slotted holes to accommodate the osteosynthesis screws or tacks in a preferred position related to the adjacent dental roots.

20 Claims, 5 Drawing Sheets

U.S. PATENT DOCUMENTS

| | | | | |
|---|---|---|---|---|
| 597,582 A | | 1/1898 | Knapp | |
| 3,454,001 A | * | 7/1969 | Stockfisch | 606/54 |
| 3,473,528 A | | 10/1969 | Mishkin et al. | |
| 4,144,643 A | | 3/1979 | Krygier | |
| 4,308,863 A | | 1/1982 | Fischer | |
| 4,386,603 A | * | 6/1983 | Mayfield | 606/105 |
| 4,445,513 A | * | 5/1984 | Ulrich et al. | 606/86 A |
| 4,730,608 A | * | 3/1988 | Schlein | 606/57 |
| 4,848,368 A | * | 7/1989 | Kronner | 606/57 |
| 5,147,358 A | * | 9/1992 | Remmler | 606/57 |
| 5,564,920 A | | 10/1996 | Klapper et al. | |
| 5,575,790 A | * | 11/1996 | Chen et al. | 606/60 |
| 5,769,850 A | | 6/1998 | Chin | |
| 5,885,283 A | * | 3/1999 | Gittleman | 606/57 |
| 5,885,290 A | * | 3/1999 | Guerrero et al. | 606/71 |
| 5,902,304 A | * | 5/1999 | Walker et al. | 606/71 |
| 5,993,448 A | | 11/1999 | Remmler | |
| 6,206,882 B1 | | 3/2001 | Cohen | |
| 6,267,589 B1 | | 7/2001 | Farzin-Nia et al. | |
| 6,328,745 B1 | | 12/2001 | Ascherman | |
| 7,588,579 B2 | * | 9/2009 | Mommaerts | 606/105 |
| 2002/0031741 A1 | * | 3/2002 | Williams | 433/19 |
| 2003/0050641 A1 | | 3/2003 | Mommaerts | |

FOREIGN PATENT DOCUMENTS

| | | |
|---|---|---|
| DE | 1049533 | 1/1959 |
| EP | 0846446 | 6/1998 |
| EP | 0706349 | 8/1999 |
| WO | WO 96/28110 | 9/1996 |
| WO | WO 96/29964 | 10/1996 |
| WO | WO 98/10708 | 3/1998 |

OTHER PUBLICATIONS

"Thread". Merriam-Webster Online Dictionary [online], [retrieved on Nov. 9, 2006], Retrieved from the Internet <URL: www.m-w.com.

English Abstract of WO 96/28110 dated Sep. 19, 1996.

English Abstract of WO 98/10708 dated Mar. 19, 1998.

Mommaerts, M.Y. "Transpalatal distraction as a method of maxillary expansion" British Journal of Oral and Maxillofacial Surgery (1999) 37, pp. 268-272.

* cited by examiner

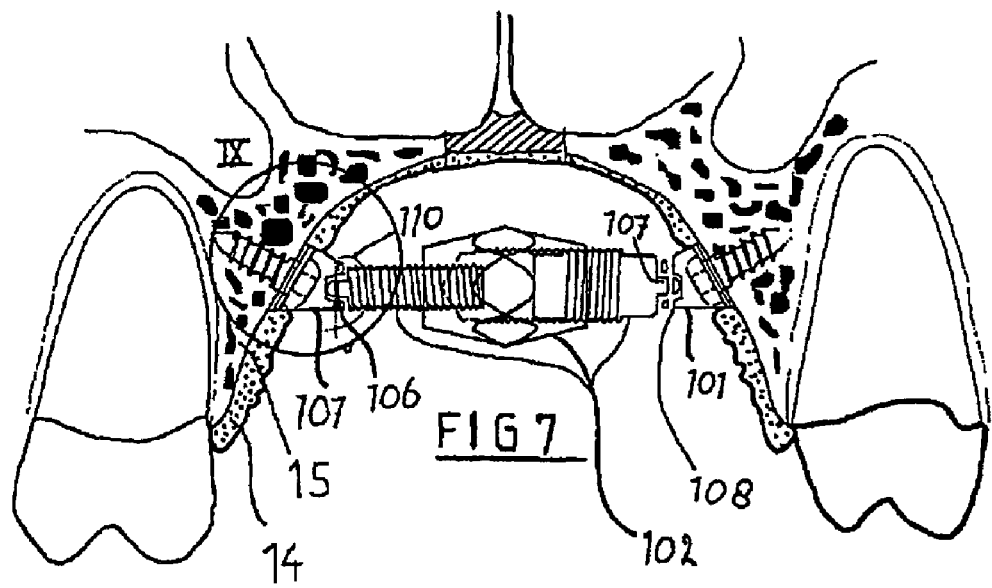
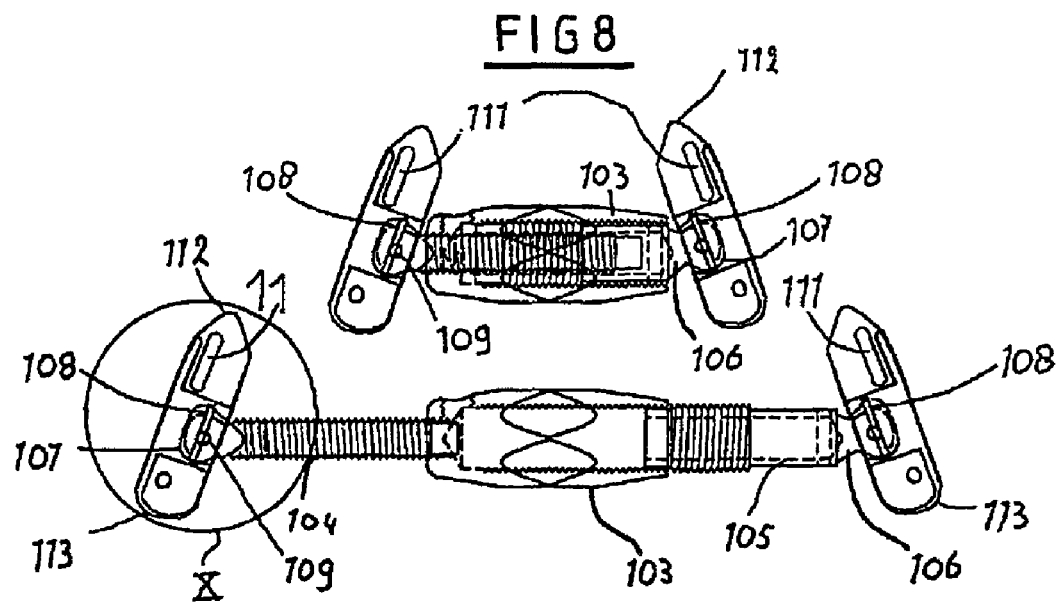

APPARATUS FOR INTRAORAL DISTRACTION OSTEOTOMY TO WIDEN THE UPPER JAW

CROSS REFERENCE TO RELATED APPLICATIONS

This application is a continuation application of Ser. No. 11/070,862 filed Mar. 2, 2005 which is a Continuation-in-part of U.S. patent application Ser. No. 10/193,695, filed Jul. 11, 2002, which application is a continuation of International patent application PCT/EP01/00398, filed Jan. 11, 2001, which are hereby incorporated in their entirety by reference.

BACKGROUND

The present invention pertains to a distraction device used to widen an upper jaw (maxillae) after cortical osteotomy and fixation of an adjustable bridging onto the bone of the palate with the goal to increase the distance between the two mutually opposite halves of the jaw by means of gradual expansion.

In addition, the present invention relates to an improved orthopaedic system wherein the device is used intra-orally in a patient to achieve a change in transverse position of two upper jaw halves or segments in relation to each other.

The device is used in maxillofacial surgery, in particular in orthognathic surgery in patients with too narrow maxillae or upper jaw. It concerns a developmental disturbance, sometimes congenital as in cleft lip and palate, which can lead to a cross-bite, tooth crowding, hindered nasal breathing, a disturbed occlusion with the lower dental arch, and a psychosocial aesthetic problem. The aim of the invention is to restore the dental occlusion, to improve nasal breathing and to bring the face into normal proportions.

SUMMARY

From one aspect, the invention provides a Distraction apparatus for expansion of an upper jaw bone after osteotomy by application of distraction forces directly to a bone of a palate with the aim to reconstruct the jaw by increasing a distance between two opposing bone segments by means of gradually stretching, comprising a distraction module having two outer ends located at a mutual distance from each other, wherein said mutual distance can be altered by means of an expansion screw in the distraction module, and two abutment plates adapted for being fixed directly to a surface of the bone of the palate, said surface facing an oral cavity, wherein said abutment plates are provided with an extension for extending into the oral cavity, wherein said extensions of the abutment plates are hingedly connected to the respective ends of the distraction module, wherein the ends of the distractor module are disk-shaped or flat.

In one embodiment, the ends have a convex disk end edge. In a further development hereof, the end edge is circular.

In one embodiment, the disk has two opposite planes that are parallel to one another.

In one embodiment, the ends are widened with respect to an arm portion connection to the arm ends.

The disk-shaped ends may merge into the distraction module via a neck.

In one embodiment, the extension forms a receiving space for receipt of the disk-shaped ends of the distraction module.

The receiving space may have two opposite walls that face the main planes of the disk shaped ends and diverge from one another in a direction towards the distraction module.

The disk-shaped ends may merge into the distraction module via a neck, wherein the extension forms a receiving space for receipt of the disk-shaped ends of the distraction module, wherein the receiving space has an opening which is narrowed with respect to the receiving space and adapted to accommodate the neck.

From a further aspect, the abutment plates may comprise base plates which are provided with at least one hole for a fastener, said base plates being malleable at least in areas thereof adjacent the extension.

From a further aspect, the abutment plates may comprise base plates which are provided with at least two holes for fasteners, a first hole being an elongated hole and a second hole being circular, wherein said holes are arranged on either side of the extension.

From a further aspect, the abutment plates may comprise base plates, said base plates having an anterior end that is pointed. The base plates may have a posterior end that is blunt.

In one embodiment, said base plates have an anterior end that is pointed and wherein said elongated hole is located at the anterior side of the extension.

From another aspect, the abutment plates may have one end that is sharp and triangular in shape so as co dissect automatically between the mucoperiosteum and the bone and another end that is blunt as to prevent damage to palatal blood vessels. From another aspect, the ends of said distraction module can be provided with a first hole and wherein said extensions are provided with a second hole, said first and second holes being for passage of a connector adapted to connect the distractor module end to the extension. The connector may be a thread or wire or the like.

In addition, the extensions may be box-shaped and may contain slit-like openings (8) to accommodate a wire or suture (10) that passes also through an opening (9) in the disk-shaped end of the arm, allowing for arming the device before osteosynthesis.

From another aspect, the invention provides a distraction apparatus for expansion of an upper jaw bone after osteotomy by application of distraction forces directly to a bone of a palate with the aim to reconstruct the jaw by increasing a distance between two opposing bone segments by means of gradually stretching, comprising a distraction module having two outer ends located at a mutual distance from each other, wherein said mutual distance can be altered by means of an expansion screw in the distraction module, and two abutment plates adapted for being fixed directly to a surface of the bone of the palate, said surface facing an oral cavity, wherein said abutment plates are provided with an extension for extending into the oral cavity, wherein said extensions of the abutment plates are hingedly connected to the respective ends of the distraction module, and wherein the abutment plates comprise malleable base plates which are provided with at least one hole for a fastener, said base plates being malleable at least in areas thereof adjacent the extension.

From yet another aspect, the invention provides a distraction apparatus for expansion of an upper jaw bone after osteotomy by application of distraction forces directly to a bone of a palate with the aim to reconstruct the jaw by increasing a distance between two opposing bone segments by means of gradually stretching, comprising a distraction module having two outer ends located at a mutual distance from each other, wherein said mutual distance can be altered by means of an expansion screw in the distraction module, and two abutment plates adapted for being fixed directly to a surface of the bone of the palate, said surface facing an oral cavity, wherein said abutment plates are provided with an extension for extending into the oral cavity, wherein said extensions of the abutment plates are hingedly connected to the respective ends of the distraction module, wherein said ends of said distraction module are provided with a first hole and wherein said extensions are provided with a second hole, said first and second holes being for passage of a connector adapted to connect the distractor module end to the extension. The connector may be releasable for temporarily use. The connector may be wire- or thread-shaped.

From still another aspect, the invention provides a distraction apparatus for the expansion of an upper jaw bone after osteotomy by application of distraction forces directly to a bone of the palate with the aim to reconstruct the jaw by increasing the distances between two opposing bone segments by means of gradually stretching, comprising a distraction module having two outer ends located at a mutual distance from each other, wherein said mutual distance can be altered by means of an expansion screw in the distraction module, and two abutment plates that can be fixed directly to a surface of the bone of the palate, said surface facing an oral cavity, wherein said abutment plates are provided with an extension, wherein said extensions have a design that allows fixation of a respective end of the distraction module onto or into the extension of the abutment plates, wherein said ends of said distraction module and said extensions are provided with first and second connecting means hingingly interengaging each other for said fixation, wherein the abutment plates comprise base plates, said base plates having an anterior end that is pointed and/or having a posterior end that is blunt.

In one further embodiment, the abutment plates may comprise base plates which are provided with at least two holes for fasteners, a first hole being an elongated hole and a second hole being circular, wherein said holes are arranged on either side of the extension, wherein said elongated hole is located at the anterior side of the extension.

From another aspect, the invention provides a method for widening an upper jaw bone (maxillae) after osteotomy, using a distraction apparatus comprising two abutment plates and a distraction module, said abutment plates each being provided with a base plate and an extension, said distraction module having two opposite ends, wherein said extensions and said distraction module ends are shaped for interengagement, wherein the distraction apparatus is placed into an oral cavity with the distraction module ends and the extensions interengaging one another and being temporarily secured to one another, wherein the abutment plates are fixed directly to bone of the palate on either side of a split in the bone of the palate by means of said base plates, said extensions piercing through palatal soft tissue into the oral cavity, whereafter the distraction module is expanded to exert a force on the extensions biasing the abutment plates away from one another and the temporarily securement is released.

From another aspect, the invention provides a distraction apparatus for expansion of an upper jaw bone after osteotomy by application of distraction forces directly to a bone of a palate with the aim to reconstruct the jaw by increasing a distance between two opposing bone segments by means of gradually stretching, comprising a distraction module having two outer ends located at a mutual distance from each other, wherein said mutual distance can be altered by means of an expansion screw in the distraction module, and two abutment plates adapted for being fixed directly to a surface of the bone of the palate, said surface facing an oral cavity, wherein said abutment plates are provided with an extension for extending into the oral cavity, wherein said extensions of the abutment plates are hingedly connected to the respective ends of the distraction module.

In one embodiment, said ends of the distraction module are conical.

The extensions may be provided with a female sleeve in which the conical end of the distraction module fits.

In one embodiment, the ends of the distraction module hingingly abut the extensions of the abutment plates.

From a further aspect, the invention provides a distraction apparatus for the expansion of the upper jaw with application of the forces directly to the palatal bone with the aim to reconstruct the jaw by increasing the distances between the two opposing bone segments by means of gradual stretching characterised in that it has the following parts:
  two abutment plates, that are fixed directly to the palatal shelves and which allow to fit of a disk-shape male wing of a distraction module into hollowed-out shaped female openings in the box-like extensions on their base-plate;
  expansion screws, called distraction modules, of different lengths, with expansion arms provided with in plane, disk-shaped male wings, straight in cross-section.

The invention further provides an embodiment in which the device has following parts:
  distraction modules of increasing lengths, with at both sides extending arms with disk-like wings that fit into the hollowed side walls of the extension boxes on the abutment plates. The disk-like extensions are in the plane of the rods and have a hole to accommodate a wire or suture;
  two abutment plates, that are fixed to the palatal shelves, with a screw into a slotted hole at one side of the extension box and a screw in a round hole at the other end of the box;
  a box-like extension, provided by a slot to fit the male wing of the expansion arms of the distraction module into; the box-like extension has a slit or opening in its upper and/or lower wall, parallel to the base-plate, situated at the level of the hole in the disk-like extension, to accommodate a wire or suture;
  a base-plate that is malleable in the area next 5 to the box-like extension.

The distraction module may comprise a mechanical jack-screw, which comprises three parts which fit into one another, the central segment having the largest diameter, and being provided at its ends with internal turns of opposite direction and different sizes, into which two mutually opposite telescopic arms fit, which are able to move into one another and can move completely into and out of the central connecting sleeve. The telescopic arms may have virtually the same length as the connecting sleeve.

The wings at the ends of the telescopic arms allow the distraction module to be fitted into the extension boxes of the abutment plates. The wings can be shaped in the form of a half or complete disk, in plane with the arms. In cross-section, the disks can be straight. They can have an opening to accommodate a wire or suture that passes also in a slotted hole or opening in the boxlike extension of the abutment plate, allowing assembly before fixation on the palatal shelf. The abutment plates can have malleable base-plates with a circular and slotted hole for improved positioning related to the dental roots. The first side walls of the boxlike extension are hollowed in the palatal plane section, as to accommodate part of the circumference of the disk-like extensions of the distractor arms. The second side walls diverging from each other in direction towards the distraction module, so that the opening in the box is depouille in the frontal section, providing a degree of freedom for the wings to be accommodated according to the slope angle of the palatal shelves. The largest width of the wings is smaller than the width of the opening of the boxes, so that the module can be easily placed and removed during (re)placement. Due to the convex shape of the side edges of the wings, the wings engage in the hollowed first side walls of the box. When the distraction module assumes an inclined orientation, the wings will rotate within the boxes and remain therein, in spite of the possible presence of increased forces.

The increased fit of the expansion arms into the box-like extensions allows oblique placement and reducing inadvertent loss of the distraction module. This is in particular advantageous in cleft palate patients.

The male wings of the expansion arms of the distractor modules provide a reduced risk to dislocate from the female slots in the box-like extensions on the abutment plates, that the components can be assembled with a wire or suture before osteosynthesis (hence reducing considerably operating time especially for novice surgeons), that the anterior end of the abutment plates dissects by itself between the mucoperiosteum and the bony surface, that the posterior end of the abutment plates is blunted to prevent damage to the palatal blood vessels, that one of the openings for the osteosynthesis screws is a "long hole", hence allowing positional adjustment related to the dental structures, and that the base plate is made malleable to accommodate surface anatomy and to prevent stripping of the bone thread.

From a further aspect, the invention provides a distraction apparatus for the expansion of the upper jaw with application of the forces directly to the palatal bone with the aim to reconstruct the jaw by increasing the distances between the two opposing bone segments by means of gradual stretching characterised in that it has the following parts:

two abutment plates, that are fixed directly to the palatal bone and of which an extension pierces through the palatal soft tissue into the oral cavity, having a design that allows fixation of the end of a distraction module;

expansion screws, called distraction modules, of different lengths, with bores for blocking screws.

In one embodiment the device has following parts:

two abutment plates, that are fixed to the palatal bone (processus palatinus ossis maxillaris), with screws into drill holes (in one embodiment) or with other means such as pins, left and right under the soft tissues;

a box-like extension provided by a slot (in one embodiment) or other hinge mechanism to fit or fix the distraction module into or onto. The extension pierces the soft tissues;

expandable parts (distraction modules) of different, increasing lengths, in one embodiment four, with at both sides connections possibilities (such as wings) that fit into or onto the extension of the abutment plates.

In one embodiment, the distraction module comprises a telescopic screw, called the distraction module. The telescopic screw allows the distraction section to be kept compact, leading to a greater stretching with a small initial length. Modules of different initial and final lengths allow to choose in the individual case for the proper initial size, and to change for a bigger size when deemed necessary.

The screws used to fix the abutment plate in the palate have appropriate lengths in order to avoid damage to the roots of the teeth.

After a latency period of four to seven days, activation can start, by ⅓ mm daily. After a distraction period of one to two weeks, and a stabilisation period of one to three months, the orthodontist can start with fixed orthodontic appliances. One or two months later, the distractor is removed. Complete bony consolidation occurs in the median vertical distraction area and in the lateral horizontal distraction areas.

The flat conical shaped wing (in one embodiment) at one of the sides of the telescopic arm allows the distraction module to be fitted into the extension box of the abutment plate.

A colour or form code on the connecting sleeve allows to control the speed of the gradual stretching.

Three bores with thread at one side of the connecting sleeve allow to block the movements of the module with a blocking screw.

The apparatus can be made of titanium. This material is well known for its optimum biocompatibility, both for incorporation into the bone (osteointegration) and for incorporation into the soft tissue parts. No allergies to titanium have been described. Dimetalosis has been ruled out. The complete device and the fixation screws may consist of titanium.

An aspect of the invention is the application of the expansion force directly onto the bone, and not indirectly over the teeth.

Assets of this invention compared to tooth-borne appliances (that are patented by Leone, Schellino and Modica (EP 0846446), by Palmisano (WO 9629964), by Bernhard Forster (WO 9628110 and WO 9810708), by Klapper and George (EP 0706349), can be that there is no or less rotation of the jaw segments in the frontal plane by its high level of force application, that it results in orthopaedic and not orthodontic expansion, that dento-alveolar relapse is not to be expected during and after the expansion, that the interchangeable expansion-modules allow to continue expansion without having to resort to the fabrication of a new appliance, and that the orthodontist has all teeth available to start with active orthodontic treatment before the stabilisation period has ended.

These and other features of the invention will emerge from the following description, in which reference is made to the appended drawings, which show an exemplary embodiment of an apparatus according to the invention.

The above-mentioned aspects can be applied separately or in combination.

BRIEF DESCRIPTION OF THE DRAWINGS

FIG. 7 shows a front view, looking from outside the mouth inwards of a second embodiment of a distraction apparatus in the extended position on the palate according to the invention on a scale of 2:1;

FIG. 8 shows a top view of an apparatus in a contracted and extended position.

DETAILED DESCRIPTION OF ILLUSTRATIVE EMBODIMENTS

In these figures, identical numerals refer to identical or similar elements.

A distraction osteotomy is a surgical operation for correcting deformity or curvature of a bone which is curved or too short, the bone being split into at least two bone segments being joined together again by dynamic osteosynthesis, that is to say gradual repositioning and fixation of the bone segments with the aid of guided rods, small metal plates, screws, pins, bone pegs or hoops.

The distraction apparatus' depicted in the figures serves to widen the upper jaw, after a cortical mono- or bilateral horizontal osteotomy and a vertical median or paramedian osteotomy, or when the patient is young enough, by expanding the median suture without additional corticotomies/osteotomies. In FIGS. 1-6, a first embodiment of the invention is depicted.

Figure 1:
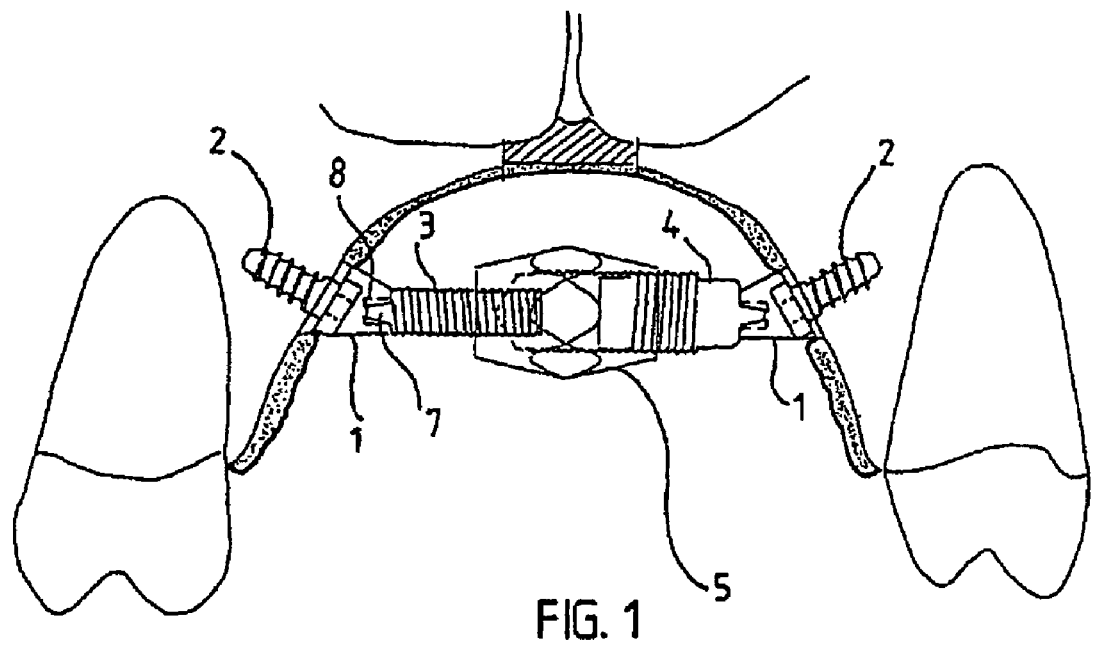
FIG. 1 shows a front view, looking from outside the mouth inwards of a first embodiment of a distraction apparatus in the extended position on the palate according to the invention on a scale of 2:1.
Figure 2:
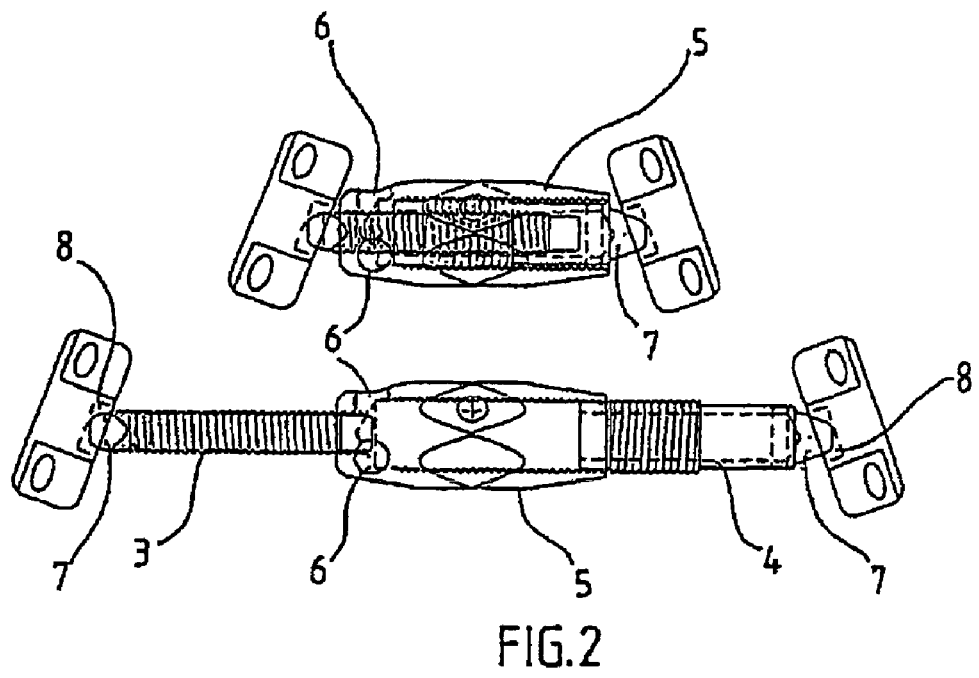
FIG. 2 shows a top view of an apparatus in a contracted and extended position.
Figure 3:
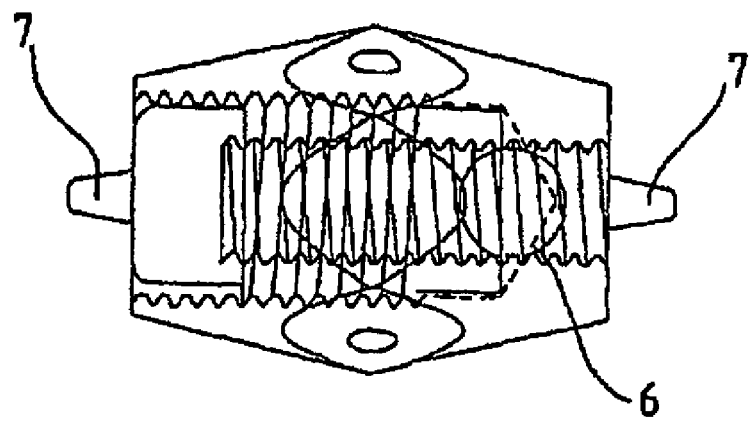
FIG. 3 shows a frontal view of a distraction module in a contracted position on a scale of 4:1.
Figure 4:
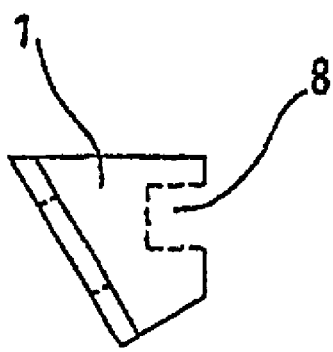
FIG. 4 shows a side view of an abutment plate with box extension on a scale of 4:1.
Figure 5:
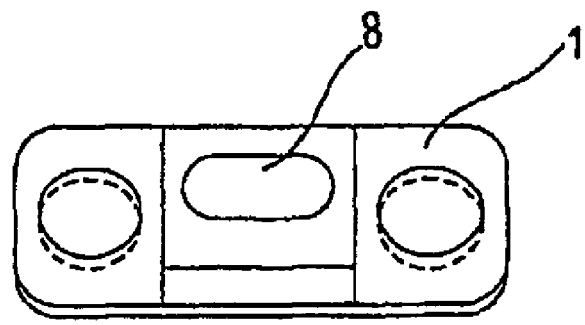
FIG. 5 shows a top view of an abutment plate with an extension on scale 4:1.
Figure 6:
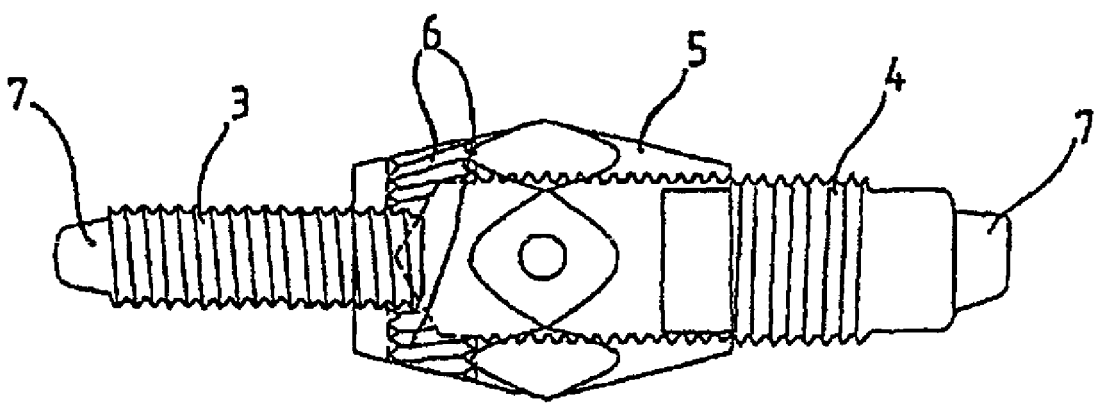
FIG. 6 shows the top view of a distraction module in extended position on a scale of 4:1.
Figure 9:
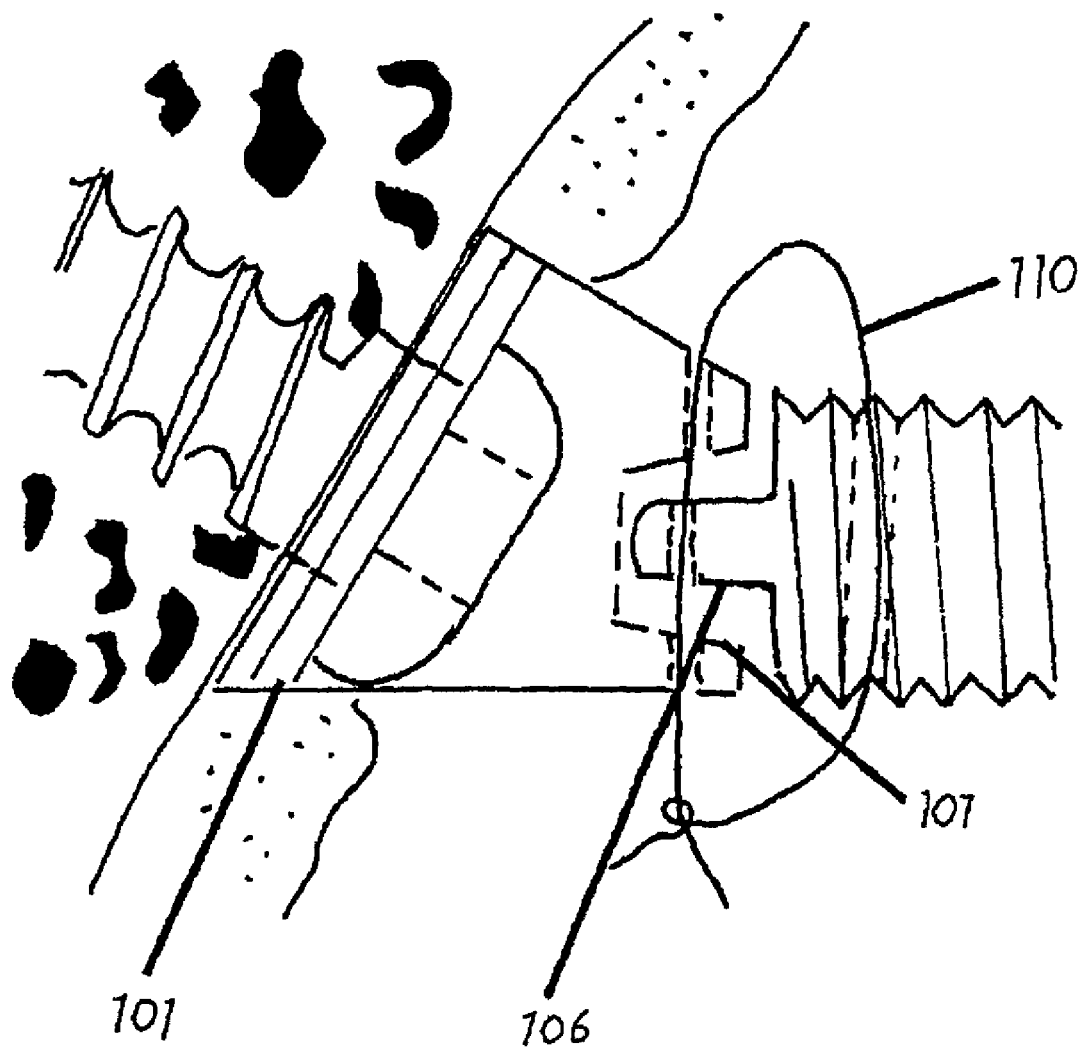
FIGS. 9 and 10 show details of FIGS. 7 and 8, respectively.
Figure 10:
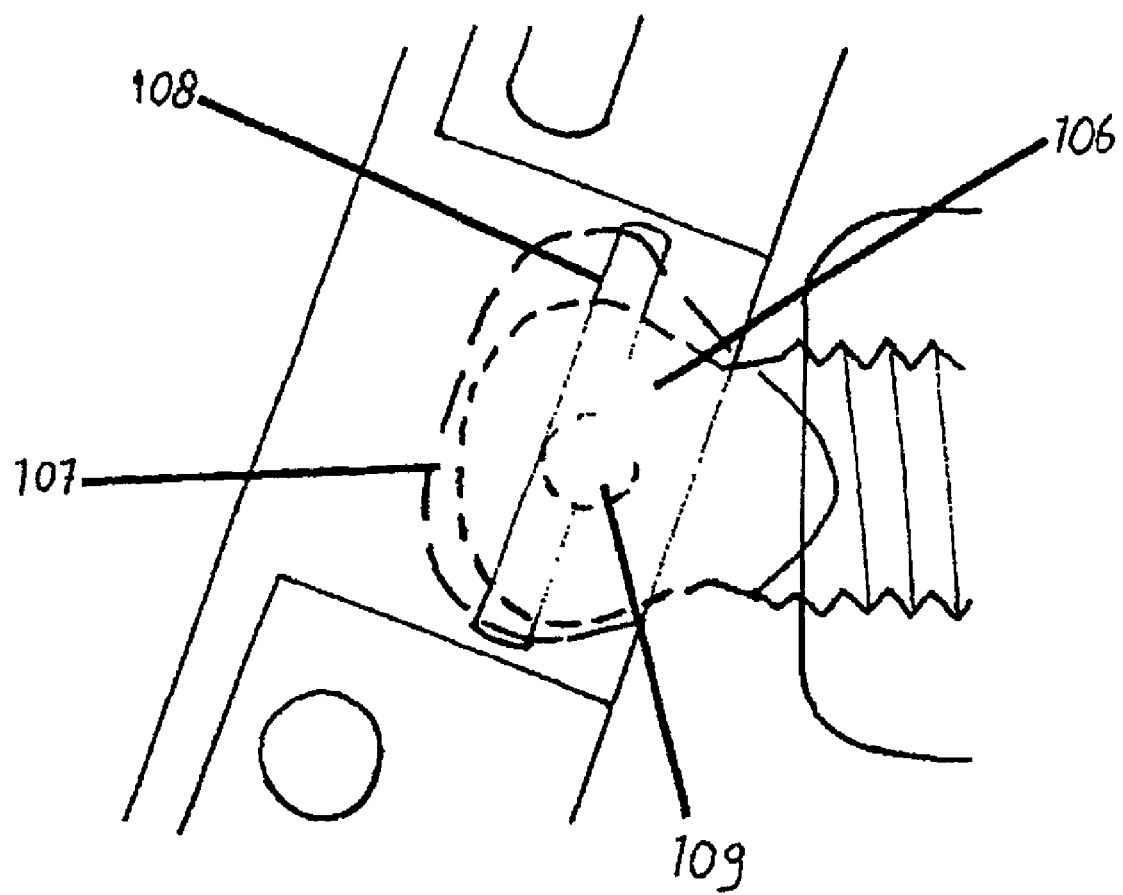

The distraction apparatus depicted in FIG. 1 serves to widen the upper jaw, after a cortical bilateral horizontal osteotomy and a vertical median osteotomy. It comprises the following parts:
two abutment plates 1, fixed with screws or pins on the palatal bone (processus palatinus ossis maxillaris) left and right of the midline;
a distraction module, depicted in FIGS. 3 and 6, in different lengths.

The distraction module is a mechanical jackscrew consisting of three parts which fit into one another. The central one has the largest diameter, in order to act as a connecting sleeve 5 and is provided at its ends with internal threads of opposite direction and different sizes, into which two mutually opposite telescopic arms 3, 4 fit, which are able to move into one another and have virtually the same length as the central connecting sleeve 5, so that they can move completely into and out of the connecting sleeve.

The connecting sleeve 5 has three bores with internal thread 6 to receive a blocking screw.

The free ends of the telescopic arms bear a male conical wing 7, fitting into the female sleeve 8 of the abutment plates 1, in this example.

In FIGS. 7-10, a second embodiment of the invention is depicted.

The distraction apparatus of FIG. 7 comprises the following parts:
two abutment plates 101, fixed with screws, tacks or pins on the maxillary palate or the palatal bone, left and right of the midline;
a distraction module 102, in different lengths.

The distraction module is a mechanical jackscrew consisting of three parts which fit into one another. The central one has the largest diameter, in order to act as a connecting sleeve 3 and is provided at its ends with internal threads of opposite direction and different sizes, into which two mutually opposite telescopic arms 104, 105 fit, which are able to move into one another.

The free ends of the telescopic arms bear a male wing 6, fitting into the female sleeve 107 of the abutment plates 101. The male wings 6 have the shape of a disk, circular or semicircular, fitting in the hollowed-out side walls of the sleeve 107 in the box-like extensions on the abutment plates. The curved edge of the disks may extend over more than 180 degrees, for instance over approximately 245 degrees, as depicted. A neck region has been formed at the transition area of the wings to the threaded arm portion.

The box-like extensions are provided with slit-like openings 108 on the caudal and/or cranial side, at the level of an opening 109 in the disk-like extension 106 of the expansion arm 104, 105 to accommodate a wire or suture 110, in order to assemble the distractor components into one unit before fixation on the bone. The hollowed side walls of the box-like extensions more or less correspond to the curved edge of the disks and extend to the neck region of the arm ends in the opening area of the box, yet allowing insertion and removal of the disks into and from the box-like extensions, if desired.

The wings of the abutment plate 1 are malleable to accommodate local surface anatomy and to prevent stripping of the bony thread. The wings are provided by at least one slotted hole 111 to accommodate local dental root anatomy;

The abutment plates 102 have at one end a triangularly shaped, self dissecting end 112, which slips between mucoperiosteum 14 and bone 15 as a dissecting instrument. The other end 113 is rounded and blunted to avoid damage to the palatal blood vessels.

What is claimed:

1. A distraction apparatus for expansion of an upper jaw bone after osteotomy by application of distraction forces directly to a bone of a palate with the aim to reconstruct the jaw by increasing a distance between two opposing bone segments by gradually stretching, the distraction apparatus comprising:
a distraction module having two outer ends located at a mutual distance from each other;
an expansion screw in the distraction module, the expansion screw configured to alter said mutual distance; and
two abutment plates that are non-integrally formed with the distraction module and have a bone contacting surface and are adapted for being fixed directly to a surface of the bone of the palate, wherein said abutment plates are provided with extensions that extend away from the bone contacting surface,
a receiving sleeve formed by the extensions of each abutment plate, said sleeve having side walls, and designed to rotatably and hingeably receive the distraction module ends,
wherein the ends of the distraction module are hingeably and releasably connected to the receiving sleeves of the abutment plates to allow movement of the abutment plates relative to the distraction module in the forward, backward, upward, and downward directions;
wherein the abutment plates comprise base plates which are provided with at least one hole for a fastener, said base plates being malleable at least in areas thereof adjacent the extension; and
wherein the ends of the distraction module can be removed from the receiving sleeves of the plates by rotating the expansion screw.

2. The distraction apparatus according to claim 1, wherein the distraction module outer ends are widened with respect to an arm portion connection to the ends.

3. The distraction apparatus according to claim 1, wherein the distraction module outer ends merge into the threaded arm portions of the distraction module via a neck, the necks having a smaller cross-sectional area than the threaded arm portions.

4. The distraction apparatus according to claim 3, wherein the receiving sleeve further comprises side walls that extend to an area proximate the neck of the distraction module.

5. The distraction apparatus according to claim 1, wherein the distraction module outer ends merge into the distraction module arms via a neck, and wherein the receiving sleeve has an opening with a narrow end adapted to accommodate the neck.

6. The distraction apparatus according to claim 1, wherein the base plates are provided with at least two holes for fasteners, a first hole being an elongated hole and a second hole being circular, wherein said holes are arranged on either side of the extension.

7. The distraction apparatus according to claim 6, wherein the base plates have an anterior end that is pointed and wherein said elongated hole is located at the anterior side of the extension.

8. The distraction apparatus according to claim 1, wherein the base plates have an anterior end that is pointed.

9. The distraction apparatus according to claim 1, wherein the base plates have a posterior end that is blunt.

10. The distraction apparatus according to claim 1, wherein the abutment plates have one end that is sharp and triangular in shape so as to dissect automatically between the mucoperiosteum and the bone and another end that is blunt as to prevent damage to palatal blood vessels.

11. The distraction apparatus according to claim 1, wherein the distraction module outer ends are provided with a first hole and wherein the extensions are provided with a second hole, the first and second holes being aligned for passage of a connector adapted to connect the distraction module outer end to the extension.

12. The distraction apparatus according to claim 1, wherein the distraction module outer ends are provided with a hole and wherein the extensions contain slit-like openings designed to be aligned with the outer end hole when the device is assembled to accommodate a wire or suture that passes through the hole and the slit-like openings, allowing for arming the device before osteosynthesis.

13. The distraction apparatus according to claim 1, wherein the outer ends of the distraction module comprise a shape selected from the group of conical-shaped, flat, and disk-shaped.

14. The distraction apparatus according to claim 1, further comprising:
   an opening through each distraction module outer end;
   slit-like openings through the extensions of each abutment plate, the slit-like openings of each abutment plate aligning with the opening of one of the distraction module outer ends;
   a first and second connector, the first connector extending through the slit-like opening of the extension of one of the abutment plates and through the opening in the outer end of one of the arms, and the second connector extending through the slit-like opening of the extension of the other abutment plate and through the opening in the outer end of the other; and
   wherein the connectors allow assembly of the abutment plates to the distraction module before fixation to the bones of the palate.

15. The distraction apparatus according to claim 14, wherein the connectors comprises a wire or a suture for temporary securing of the outer ends of the distraction module to the extensions of the abutment plates.

16. A distraction apparatus for expansion of an upper jaw bone after osteotomy by application of distraction forces directly to a bone of a palate with the aim to reconstruct the jaw by increasing a distance between two opposing bone segments by gradually stretching, the distraction apparatus comprising:
   a distraction module having a connecting sleeve having internal threads at opposite ends for receiving two threaded arm portions of arms having external threads and extending in opposite directions, two outer ends at distal ends of the arms and located at a mutual distance from each other, the outer ends having a conical shaped edge,
   an expansion screw in the distraction module, the expansion screw configured to alter said mutual distance, and
   two abutment plates that are non-integrally formed with the distraction module and that have a bone contacting surface, and are adapted for being fixed directly to a surface of the bone of the palate, wherein said abutment plates are provided with extensions that extend away from the bone contacting surface, the extensions defining a receiving sleeve designed to rotatably and hingeably receive the conical-shaped end of the distraction module, wherein said extension of the abutment plates are configured to hingedly connect to the respective ends of the distraction module,
   wherein said ends of said distraction module are provided with a first opening and wherein said extensions are provided with a second opening, said first and second openings being for passage of a connector adapted to connect the distraction module end to the extension,
   wherein the conical shaped edge of the outer ends and corresponding shaped edge of the receiving sleeves allow for rotational movement of the abutment plates relative to the distraction module; and
   wherein the distal end of the distraction module arms can be removed from the receiving sleeves of the plates by rotating the connecting sleeve.

17. The distraction apparatus according to claim 16, wherein the abutment plates comprise base plates, said base plates having an anterior end that is pointed.

18. The distraction apparatus according to claim 17, wherein the base plates have a posterior end that is blunt.

19. The distraction apparatus according to claim 17, wherein the base plates comprise at least two holes for fasteners, a first hole being an elongated hole and a second hole being circular, wherein said holes are arranged on either side of the extension, wherein said elongated hole is located at the anterior side of the extension.

20. The distraction apparatus according to claim 16, wherein the connecting sleeve has at least one bore with an internal thread to receive at least one blocking screw.

* * * * *